United States Patent
Rukhman et al.

(10) Patent No.: US 7,199,144 B2
(45) Date of Patent: *Apr. 3, 2007

(54) PROCESS FOR THE PREPARATION OF VALSARTAN AND INTERMEDIATES THEREOF

(75) Inventors: Igor Rukhman, Technion (IL);
Ben-Zion Dolitzky, Petah Tiqva (IL);
Evgeni Flyaks, Kiriat-Bialik (IL)

(73) Assignee: Teva Pharmaceuticals Industries, Ltd., Petah Tiqva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 10/829,873

(22) Filed: Apr. 21, 2004

(65) Prior Publication Data

US 2005/0059827 A1    Mar. 17, 2005

Related U.S. Application Data

(60) Provisional application No. 60/557,497, filed on Mar. 30, 2004, provisional application No. 60/512,557, filed on Oct. 16, 2003, provisional application No. 60/473,640, filed on May 28, 2003, provisional application No. 60/471,871, filed on May 20, 2003, provisional application No. 60/464,197, filed on Apr. 21, 2003.

(51) Int. Cl.
*A61K 31/41* (2006.01)
*C07D 257/00* (2006.01)

(52) U.S. Cl. .................... 514/381; 548/253
(58) Field of Classification Search ............ 514/381; 548/253
See application file for complete search history.

(56) References Cited

U.S. PATENT DOCUMENTS

| | | | |
|---|---|---|---|
| 5,260,325 A | | 11/1993 | Markwalder et al. |
| 5,399,578 A | * | 3/1995 | Buhlmayer et al. .......... 514/381 |
| 5,965,592 A | | 10/1999 | Buhlmayer et al. |
| 6,271,375 B1 | | 8/2001 | Villa et al. |
| 6,294,197 B1 | | 9/2001 | Wagner et al. |
| 6,395,728 B2 | | 5/2002 | Webb et al. |
| 6,465,502 B1 | | 10/2002 | Bullock et al. |
| 6,485,745 B1 | | 11/2002 | Wagner et al. |
| 2002/0132839 A1 | | 9/2002 | Ganter et al. |
| 2003/0035832 A1 | | 2/2003 | Katakuse et al. |
| 2003/0152620 A1 | | 8/2003 | Ganter et al. |
| 2003/0207930 A1 | | 11/2003 | Marti et al. |
| 2004/0072886 A1 | | 4/2004 | Reguri et al. |
| 2004/0242661 A1 | | 12/2004 | Rukhman, et al. |
| 2005/0059827 A1 | | 3/2005 | Rukhman, et al. |

FOREIGN PATENT DOCUMENTS

| | | |
|---|---|---|
| EP | 0 570 091 A1 | 11/1993 |
| EP | 0 443 983 B1 | 2/1996 |
| WO | WO 97/30036 | 8/1997 |
| WO | WO 99/001459 A | 1/1999 |
| WO | WO 99/67231 | 12/1999 |
| WO | WO 01/82858 A2 | 11/2001 |
| WO | WO 01/82858 A3 | 11/2001 |
| WO | WO 02/06253 A1 | 1/2002 |
| WO | WO 03/070246 A1 | 8/2003 |
| WO | WO 03/089417 | 10/2003 |
| WO | WO 2004026847 | 4/2004 |
| WO | WO 2004/083192 | 9/2004 |
| WO | WO 2004/087681 | 10/2004 |
| WO | WO 2004/094392 A1 | 11/2004 |

OTHER PUBLICATIONS

U.S. Appl. No. 10/802,627.*
Peter Buhlmayer, et al., *Bioorgan. & Med. Chem. Lett.*, 4(1), 29-34 (1994).
Th.Moenius, et al., *J.Labelled Cpd. Radiopharm.*, 43(13) 1245-1252 (2000).
Qingzhong Jia, et al., *Zhongguo Yiyao Gongye Zazhi*, 32(9) 385-387 (2001).
Borka L., et al., "Crystal Polymorphism of Pharmaceuticals", *Acta Pharm. Jugosl.*, 40, (1990) 71-94.
Merck Index (12$^{th}$ Edition, p. 1691, Valsartan n. 10051).
Zhong Guo, et al., *Chinese Journal of Pharmaceuticals*, 2002, pp. 385-387, vol. 32, Part 9.

* cited by examiner

*Primary Examiner*—Kamal A. Saeed
*Assistant Examiner*—Susannah L. Chung
(74) *Attorney, Agent, or Firm*—Kenyon & Kenyon LLP

(57) ABSTRACT

Provided are process for the preparation of valsartan and the precursors thereof.

18 Claims, No Drawings

PROCESS FOR THE PREPARATION OF VALSARTAN AND INTERMEDIATES THEREOF

PRIORITY

This Application claims the benefit of US provisional application Ser. No. 60/473,640, filed May 28, 2003; U.S. patent application Ser. No. 10/802,627, filed Mar. 17, 2004; PCT International Application No. PCTUS04/08322, filed Mar. 17, 2004; U.S. provisional application Ser. No. 60/557,497, filed Mar. 30, 2004; U.S. provisional application Ser. No. 60/512,557, filed Oct. 16, 2003; U.S. provisional application Ser. No. 60/471,871, filed May 20, 2003; and U.S. provisional application Ser. No. 60/464,197, filed Apr. 21, 2003, the contents of all of which are incorporated herein.

FIELD OF THE INVENTION

The present invention relates to a process for preparing valsartan and precursors thereof.

BACKGROUND

Valsartan, also known as (S)—N-(1-Carboxy-2-methyl-prop-1-yl)-N-pentanoyl-N-[2'-(1H-tetrazol-5-yl)bi phenyl-4-ylmethyl]-amine, has the following structure:

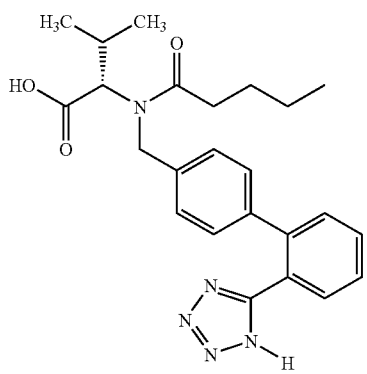

| Formula | $C_{24}H_{29}N_5O_3$ |
|---|---|
| Molecular Mass | 435.52 |
| Exact Mass | 435.227040 |
| Composition | C 66.19% H 6.71% N 16.08% O 11.02 |
| Melting Range | 105–110° C. | and is marketed as the free acid under the name DIOVAN. DIOVAN is prescribed as oral tablets in dosages of 40 mg, 80 mg, 160 mg and 320 mg of valsartan.

Valsartan and/or its intermediates are disclosed in various references, including: U.S. Pat. Nos. 5,399,578, 5,965,592, 5,260,325, 6,271,375, WO 02/006253, WO 01/082858, WO 99/67231, WO 97/30036, Peter Bühlmayer, et. al., Bioorgan. & Med. Chem. Let., 4(1) 29–34 (1994), Th. Moenius, et. al., J. Labelled Cpd. Radiopharm., 43(13) 1245–1252 (2000), and Qingzhong Jia, et. al., Zhongguo Yiyao Gongye Zazhi, 32(9) 385–387 (2001).

Valsartan is an orally active specific angiotensin II antagonist acting on the AT1 receptor subtype. Valsartan is prescribed for the treatment of hypertension. U.S. Pat. No. 6,395,728 is directed to use of valsartan for treatment of diabetes related hypertension. U.S. Pat. Nos. 6,465,502 and 6,485,745 are directed to treatment of lung cancer with valsartan. U.S. Pat. No. 6,294,197 is directed to solid oral dosage forms of valsartan.

The synthesis of valsartan is discussed, inter alia, in U.S. Pat. No. 5,399,578. In the synthesis disclosed therein, the final synthetic step (exclusive of work-up and purification) involves the reaction of a cyano group on the biphenyl ring with an azide, for example, tributyl tin azide. The reaction scheme of the '578 patent is as follows:

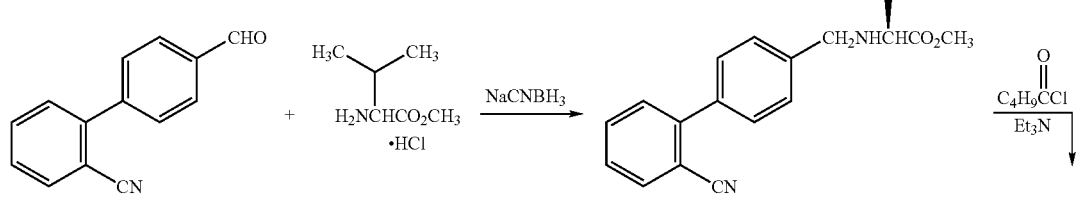

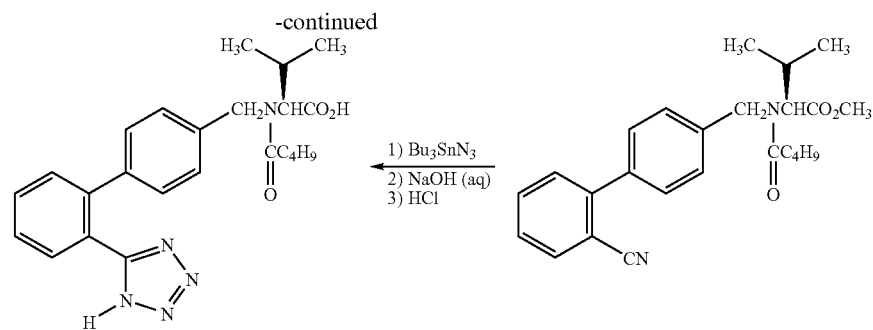
The starting compound in the '578 patent is made as follows:
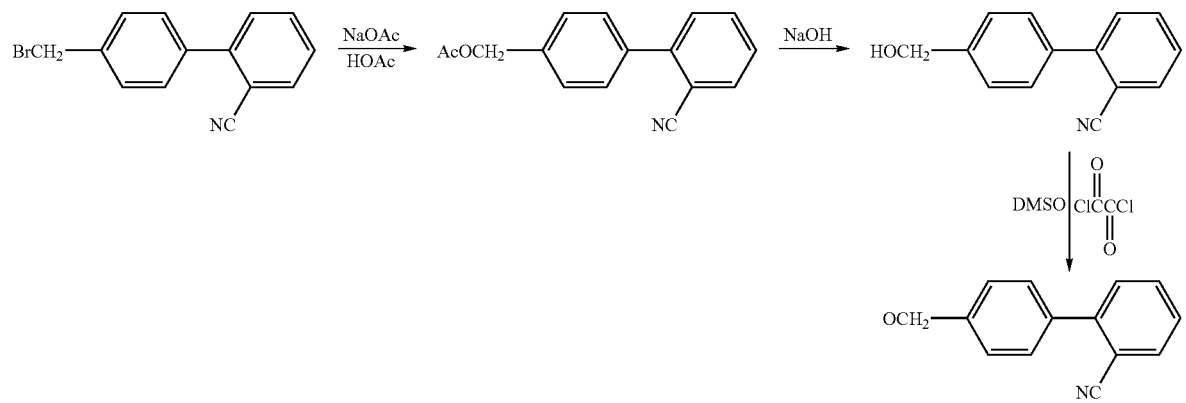
Peter Bühlmayer, et. al., Bioorgan. & Med. Chem. Let., 4(1) 29–34 (1994)
In Moenius, et. al., J. Labelled Cpd. Radiopharm., 43(13) 1245–1252 (2000), various schemes for synthesis of valsartan are provided, with one being:
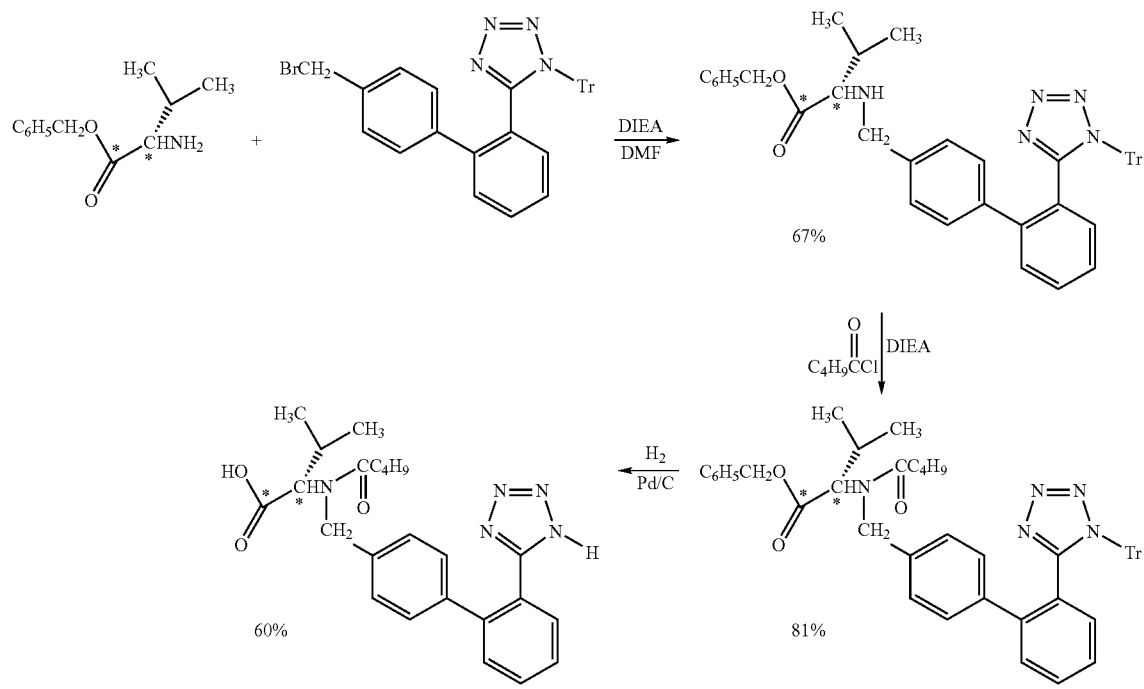

Another paper, Qingzhong Jia, et. al., Zhongguo Yiyao Gongye Zazhi, 32(9) 385–387 (2001), discloses a synthesis scheme for valsartan as follows:

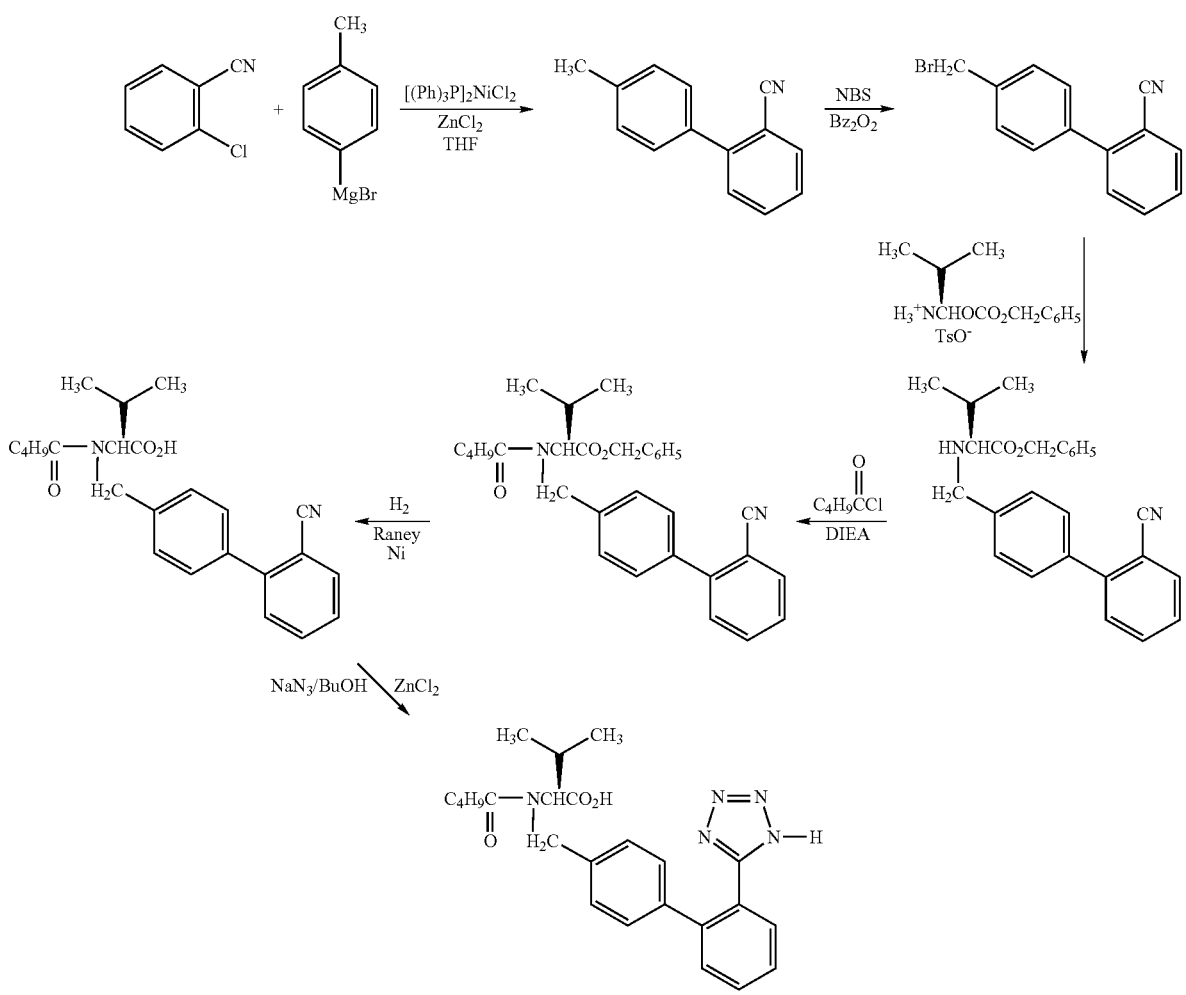

There is a need in the art for an improved synthetic process for the preparation of valsartan and precursors of valsartan.

OBJECTS AND SUMMARY OF THE INVENTION

In one aspect, the present invention provides a process for preparing valsartan containing less than about 5000 ppm residual solvent, comprising the steps of:
  a) providing valsartan containing less than about 10% organic solvent by weight; and
  b) triturating the valsartan in water.

In one aspect, the present invention provides a process for preparing valsartan containing less than about 5000 ppm residual solvent, comprising the steps of:
  a) providing valsartan containing less than about 10% organic solvent by weight; and
  b) contacting with humid air in a fluidized bed drier.

In one aspect, the present invention provides a process for preparing valsartan containing less than about 5000 ppm residual solvent, comprising the steps of:
  a) providing valsartan containing less than about 10% organic solvent by weight; and
  b) maintaining the valsartan at a temperature of from about 5 to about 60° C. under pressure of less than 30 mmHg for a period of from about 1 to 5 days.

In one aspect, the present invention provides a process for preparing compound G3:

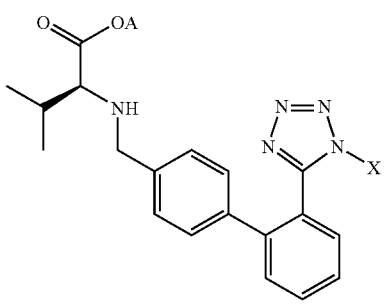

wherein A is a C1 to C4 alkyl ester and X is a trityl group, comprising the steps of:
a) reacting compound G2:

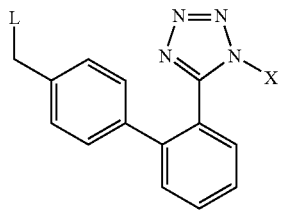

wherein L is a leaving group, with a derivative of L-valine in an organic solvent;
b) heating the reaction mixture;
c) cooling; and
d) recovering the compound G3.

In one aspect, the present invention provides a process for preparing compound G4 (shown below), comprising the steps of:
a) reacting compound G3:

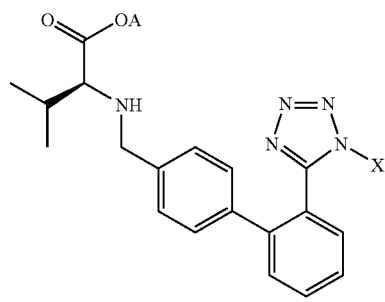

wherein A is a C1 to C4 alkyl ester and X is a trityl group, with an acylating agent in an organic solvent;
b) agitating the reaction mixture; and
c) recovering the compound G4.

In another aspect, the present invention provides a process for preparing compound G4:

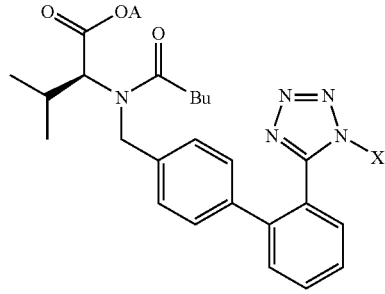

wherein A is a C1 to C4 alkyl ester and X is a trityl group, comprising the steps of:
a) reacting compound G2:

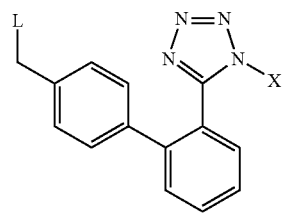

wherein X is a trityl group and L is a leaving group, with a derivative of L-valine in an organic solvent in the presence of a phase transfer catalyst;
b) heating the reaction mixture;
c) cooling;
e) adding an acylating agent;
f) agitating the reaction mixture; and
g) recovering the compound G4.

In one aspect, the present invention provides a process for preparing valsartan comprising the steps of:
a) reacting compound G2:

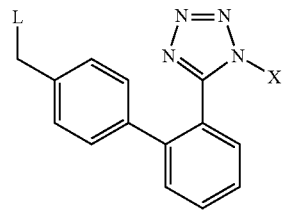

with a derivative of L-valine in a first organic solvent to obtain a compound G3:

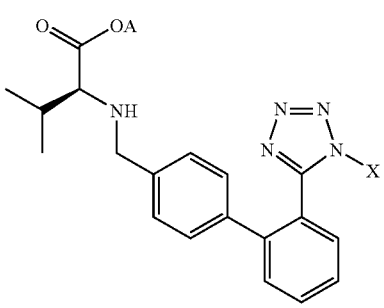

b) reacting compound G3 with an acylating agent in a second organic solvent to obtain a compound G4;

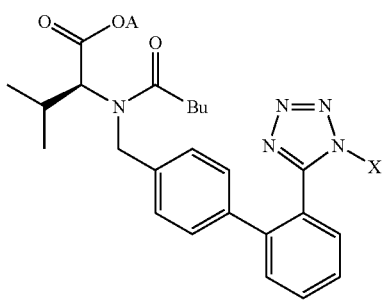

G4 and c) hydrolyzing compound G4 to obtain valsartan, wherein A is a C1 to C4 alkyl ester, X is a trityl group and L is a leaving group.

In one aspect, the present invention provides a process for preparing L-valsartan comprising the steps of:
  a) heating trityl valsartan in methanol in the absence of an acid to hydrolyze the trityl group in solution;
  b) cooling the solution to precipitate the trityl group; and
  c) recovering the L-valsartan.

In one aspect, the present invention provides a process for preparing L-valsartan from trityl valsartan comprising the steps of:
  a) stirring a heterogeneous mixture of valsartan in water and acetone;
  b) basifying the mixture
  b) removing the acetone;
  c) filtering the water to remove the trityl group;
  d) extracting the water at acidic pH with ethyl acetate; and
  e) removing the iso-butyl acetate.

In one aspect, the present invention provides a process for preparing valsartan comprising the steps of:
  a) reacting compound G2:

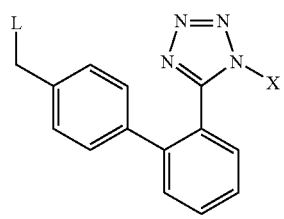

G2 wherein X is a trityl group and L is a leaving group, with a derivative of L-valine in an organic solvent;
  b) heating the reaction mixture;
  c) cooling;
  d) recovering the compound G3:

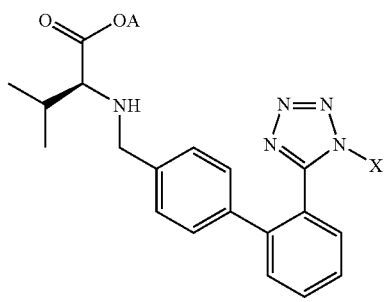

G3 wherein A is a C1 to C4 alkyl ester; and
  e) converting the product of step (d) to valsartan.

In one aspect, the present invention provides a process for preparing valsartan comprising the steps of:
  a) reacting compound G3:

G3 wherein A is a C1 to C4 alkyl ester and X is a trityl group, with an acylating agent in an organic solvent;
  b) agitating the reaction mixture;
  c) recovering the compound G4:

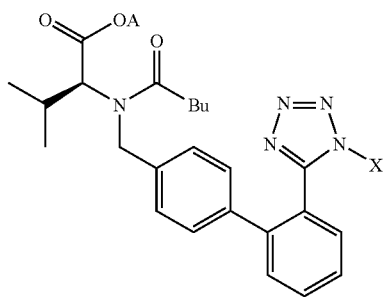

G4 and
  d) converting the product of step (c) to valsartan.

DETAILED DESCRIPTION OF THE INVENTION

As used herein, the term agitation refers to causing motion in a liquid through application of a force, such as by stirring.

As used herein, the terms 'triturating', 'slurrying' and 'suspending' are interchangeable, and all refer to a process carried out in a heterogeneous mixture where complete dissolution does not occur.

The present invention provides a process for synthesis of valsartan. In the present invention, valsartan is prepared by reacting a compound of formula G2, wherein

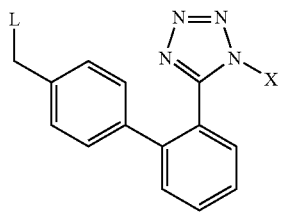

G2

X is a trityl protecting group with a $C_1$ to $C_4$ ester of valine, followed by reaction with a valeroyl halide, and hydrolysis of the resulting product to obtain valsartan.

The reaction is carried out in an organic solvent. Examples of preferred organic solvents include, but are not limited to, N,N dimethyl formamide (DMF), dimethyl acetamide (DMA), toluene, hexane, 1,2-dimethoxyethane (DME), diethoxymethane, tetrahydrofuran (THF), acetonitrile (ACN), benzene, m-xylene, ethyl acetate, o-xylene, tetralins, formals, glymes and mixtures thereof. Other hydrocarbons useful in the practice of the present invention will be apparent to the skilled artisan.

The synthesis of valsartan, of the present invention, includes the step of reacting a 5-(4'bromomethylbiphenyl-2-yl)-1H-tetrazole with an L-valine $C_1$ to $C_4$ derivative. A preferred 5-(4'bromomethylbiphenyl-2-yl)-1H-tetrazole is 5-(4'bromomethylbiphenyl-2-yl)-1-trityl-1H-tetrazole (VLS-02). A preferred L-valine ester is L-valine methyl ester (VLS-07) or t-butyl ester. The use of an alkyl ester allows for removal under relatively mild conditions, and with hydrolysis. The step is carried out in an organic solvent reaction system. To the organic solvent is added an amount of a basic material. The basic material may be a carbonate salt of an alkali metal or an organic base. Preferred salts of alkali metals include sodium carbonate and potassium carbonate. Carbonates are suitable for a process on an industrial scale since they are cheaper than organic bases such as DIEA. Preferred organic bases include triethanolamine, diethanolamine, triethylamine, di-iso propyl methylamine and diethylamine. Ethyl amine is also cheaper than DIEA. As described above the organic solvent is preferably selected from DMF, DMA, acetonitrile (ACN), toluene, hexane, DME, diethoxymethane, THF, benzene, m-xylene, o-xylene, ethyl acetate, tetralins, formals, glymes and mixtures thereof. A most preferred organic solvent is acetonitrile. The reaction may optionally be carried out in the presence of a catalyst. Preferred solvents for use with a phase transfer catalyst are toluene and ethyl acetate. VLS-07 is added to the solvent/base mixture. VLS-02 is added (preferentially in three separate portions) to the reaction mixture, and the resulting reaction mixture is heated with agitation for a reaction time of between 1 to 6 hours.

After the reaction time, the reaction system is cooled, and the solvent is removed to yield the crude residue of N-valine methyl ester 5-(4'methylbiphenyl-2-yl)-1-trityl-1H-tetrazole reaction product (VLS-04). Typically the solvent is removed by evaporation under reduced pressure.

In addition to bromine in VLS-02, other leaving groups may be utilized, including other halogens such as chlorine, or sulfonates. The acylating agent used may also include other leaving groups.

In a second step of the synthetic method of the present invention, the N-valine methyl ester 5-(4'methylbiphenyl-2-yl)-1-trityl-1H-tetrazole reaction product (VLS-04) is reacted with an acylating agent to form a valsartan precursor such as (S)—N-(1-carboxymethoxy-2-methyl-prop-1-yl)-N-pentanoyl-N-[2'-(1-trityl-1H-tetrazol-5-yl)bi phenyl-4-yl methyl]-amine (VLS-05). Crude residue produced in the synthetic step described above is dissolved in a suitable organic solvent. The organic solvent preferably contains an amount of an organic basic material. Preferred organic basic materials include triethylamine, di-iso propyl methylamine and tributylamine. Preferred organic solvents include toluene, DMA, DMF, hexane and acetonitrile. A most preferred organic solvent is dry toluene. To the resulting solution is added an acylating agent. The acylating agent is valeroyl chloride in this case. The resulting mixture is agitated at room temperature for a period of from about 12 to about 24 hours. Preferably the reaction mixture is agitated for a period of about 20 hours. The time of the acylation reaction can be conveniently monitored using thin layer chromatography. Following completion of the reaction, the reaction mixture is neutralized with a molar excess of base, preferably aqueous $NaHCO_3$, and the resulting two-phase reaction system is separated. The organic phase is washed and dried, and the reaction product, (S)—N-(1-carboxymethoxy-2-methyl-prop-1-yl)-N-pentanoyl-N-[2'-(1-trityl-1H-tetrazol-5-yl)biphenyl-4-yl methyl]-amine, (VLS-05), separated out. The separation may be carried out by any known method, but is typically carried out by evaporation under reduced pressure. The reaction product may be purified by, for example, chromatographic means, prior to further use in the synthesis. The crude material may be used in the next step.

In a third step of the synthetic method of the present invention the protecting groups, e.g., the trityl group attached to the tetrazole ring and the L-valine substituent (such as the methyl ester group of L-valine methyl ester (VLS-07)), are cleaved by hydrolysis to produce valsartan (VLS-00). Crude residue produced in the synthetic step described above is dissolved in a suitable water-miscible solvent. A solvent is water miscible if it is miscible with water at least in any proportion from 80:20 to 20:80 (weight basis). Preferred water-miscible solvents include acetone, methyl ethyl ketone (MEK), acetonitrile, tetrahydrofuran (THF), dioxane and $C_1$ to $C_4$ alcohols. Acetone is a most preferred water-miscible solvent. The resulting solution is acidified and agitated at a temperature of from about 0° C. to about 40° C. Most preferably the temperature is about room temperature. The time of the cleavage reaction can be conveniently monitored using thin layer chromatography. An aqueous solution of a basic material is added. Suitable basic materials include potassium hydroxide, potassium carbonate and sodium hydroxide. The trityl alcohol formed is separated and the liquid phase is acidified by addition of a suitable acid to a pH of about 3. Preferred acids include mineral acids, hydrogen sulfate, trifluoroacetic acid, formic acid, hydrobromic acid and acetic acid. A most preferred acid is hydrochloric acid or hydrogen sulfate. The resulting suspension is extracted with ethyl acetate and the crude product, for example, (S)—N-(1-carboxymethoxy-2-methyl-prop-1-yl)-N-pentanoyl-N-[2'-(1H-tetrazol-5-yl) biphenyl-4-yl methyl]-amine, (VLS-06), recovered by, for example, evaporation under reduced pressure. The resulting product is dissolved in an organic solvent. Preferred organic solvents include organic alcohols, acetone and acetonitrile. A most preferred solvent is methanol. The resulting solution is cooled to a temperature of between about −10° C. and about 45° C. Preferably the resulting solution is cooled to a temperature of between about 0° C. and about 4° C. The acid is neutralized with a molar excess of base, preferably aqueous KOH, and the water-miscible solvent is evaporated, preferably at reduced pressure. The time of the cleavage reaction can be conveniently monitored using thin layer chromatography or HPLC monitoring. The solution is extracted with ethyl acetate and acidified by addition of a suitable acid to a pH of about 3. Preferred acids include mineral acids, hydrogen sulfate, trifluoroacetic acid, formic acid, hydrobromic acid and acetic acid. A most preferred acid is hydrochloric acid or hydrogen sulfate. The resulting suspension is cooled and the product recovered by, for example, extraction. If desired, the isolated product can be washed with water, and dried, preferably at reduced pressure.

The use of hydrolysis to remove the trityl group allows for a process on an industrial scale, since the trityl group precipitates as tri-phenyl carbinol, and may be recycled to prepare compound G2. If the trityl group is removed by hydrogenation, the protecting group that comes off would lack a hydroxide group that allows for derivatization into a halide and reaction with the amine of the tetrazole group to obtain compound G2.

Some of the steps of the present invention may be carried out in one pot, as illustrated in the examples.

The valsartan synthesized may be obtained as various polymorphic forms in the solid state. Such forms are disclosed in Appl. No. 60/455,286, Filed on Mar. 17, 2003, entitled "Polymorphs of Valsartan and Processes for their Preparation", which is incorporated herein by reference.

Crude valsartan may be crystallized from organic solvents such as dichloromethane, diethyl ether, ethyl acetate, t-butyl acetate, acetone, methyl ethyl ketone and isopropyl methyl ketone. In a preferred embodiment, valsartan is crystallized from such $C_3$ to $C_7$ ketone and esters, with ethyl acetate being particularly preferred.

When crude material is crystallized out of ethyl acetate, the wet material contains about 17% ethyl acetate. It is believed that crystallization from other organic solvents may also result in similar amounts of the solvent.

The present invention provides for removing residual organic solvent such as ethyl acetate from the crude material. The wet valsartan, if having a high solvent content, is first dried, for example with a fluid bed dryer or a vacuum dryer, to obtain valsartan with less than about 10% organic solvent by weight. Preferably, after drying, in case of ethyl acetate, the ethyl acetate contains about 2.7% ethyl acetate by weight.

The present invention provides three different ways of removing residual organic solvent from valsartan which may not be removed by conventional drying means.

In the first embodiment, the crude valsartan containing less than about 10% residual solvent is triturated in water, in order to remove the residual solvent to acceptable levels (according to the ICH guidelines the level is limited to less than about 5000 ppm). In one embodiment, after trituration in water, the level of the residual solvent is less than about 4000, more preferably about 3600 ppm. Preferably the trituration is performed from about 4 to about 50° C., more preferably from about 25 to about 40° C. Preferably, the trituration is carried out for about 5 hours to about 48 hours, more preferably from about 3 to about 20 hours. Preferably, the volume of water is about 4 to about 20 liters per kilogram of valsartan.

Another manner to remove residual solvent, particularly ethyl acetate, is by performing a solvent exchange by contacting the solvate with humid gas in a fluidized bed apparatus. Preferably, the temperature is of about 25° C. to about 50° C., more preferably about 30° C. to about 40° C. The contacting may be carried out for preferably about 6 hours to about 2 days. As used herein, the term "humid" refers to a relative humidity of at least 30%, more preferably at least about 50% and most preferably at least about 80%. A suitable fluidized bed apparatus is Retsch TG-100.

Another manner to remove the residual solvent is by harsh drying which is carried out by maintaining the valsartan at a temperature of about 5 to about 60° C. under pressure of less than about 30 mmHg for a period of about 1 to about 5 days. Preferably, the pressure is less than about 10 mmHg, more preferably less than about 1 mmHg.

The above embodiments for solvent removal often result in a powder, which is highly amorphous in nature, but may have a low level of crystallinity.

The final material obtained in the present invention is of particular high purity. The valsartan obtained is substantially free of its D-isomer. The tablet level of the D-isomer is 0.26% area by HPLC (USP method) in the prior art. In our sample, we managed to obtain a sample with a level of <0.1% by HPLC according to USP, more preferably about 0.07% of the D-isomer.

This reduction in the level of the D-isomer was carried out without use of any special cleaning reagents. Examples 8 and 9 illustrate such cleaning effect. Without being bound by any theory, when the cleaning effect appears during the synthesis, such effect might be due to use of acetone/water. A preferred ratio of acetone to water is about 4 to about 0.5–1 (vol/vol). In examples 8 and 9, the ratio between acetone and water is 2/1, and the ratio of the acetone/water solution to trityl valsartan is 9 ml of the mixture per 1 gram of trityl valsartan; In example 11 the ratio between acetone and water 3.5/1, and the ratio of the acetone/water solution to trityl valsartan is 5 ml of the mixture per 1 gram of trityl valsartan. Cleaning with a mixture such as that of acetone and water is carried out under heterogeneous conditions, rather than a clear solution: due to a difference of solubility between the racemate valsartan and the valsartan (L-isomer), or trityl valsartan, or L-trityl valsartan. The preferred ratios of the acetone to water, and the water/acetone solution to the TVLS, are the ratios that give heterogeneous mixture, rather than a clear solution.

The cleaning effect may also happen when hydrolyzing the protecting groups in methanol in the absence of an acid. Simply, heating trityl valsartan, to reflux temperature in methanol followed by cooling may result in cleaning.

The cleaning effect may also occur when triturating crystals obtained from ethyl acetate in water to remove residual solvent.

Although the cleaning effect in the present invention is illustrated with trityl valsartan as a starting material, one of skill in the art would appreciate that the cleaning effect may be used in the same manner when having valsartan as a starting material. The valsartan can for example be a sample recovered after hydrolysis of the methyl ester and the trityl group, though preferably the ester is hydrolyzed first, and then the resulting trityl valsartan is "cleaned" according to processes of the present invention.

Pharmaceutical formulations of the present invention contain crystalline or amorphous valsartan, optionally in mixture with other form(s) of valsartan. The valsartan prepared by the processes of the present invention are ideal for pharmaceutical formulation. In addition to the active ingredient(s), the pharmaceutical compositions of the present invention may contain one or more excipients. Excipients are added to the composition for a variety of purposes.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesiumn carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, valsartan and any other solid excipients are dissolved or suspended in a liquid carrier such as water, vegetable oil, alcohol, polyethylene glycol, propylene glycol-or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or-coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate. Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages can be conveniently presented in unit dosage form and prepared by any of the methods well-known in the pharmaceutical arts.

The solid compositions of the present invention may be a plurality of valsartan particles wherein the mean particle size (d0.5) is about 2 µm to about 7 µm, and about 10 volume percent or less of the plurality of particles have a particle diameter equal to or greater than about 10 µm.

The active ingredient and excipients may be formulated into compositions and dosage forms according to methods known in the art. The solid oral dosage forms disclosed in U.S. Pat. Nos. 6,485,745 and 6,395,728 may be used as a guidance. The dosages and formulation of DIOVAN may also be used for guidance. The dosage is preferably from about 10 mg to about 1280 mg, more preferably from about 20 mg to about 640 mg, and most preferably from about 40 mg to about 320 mg.

The present invention can be illustrated in one of its embodiments by the following non-limiting examples.

EXAMPLE 1

Preparation of VLS-04

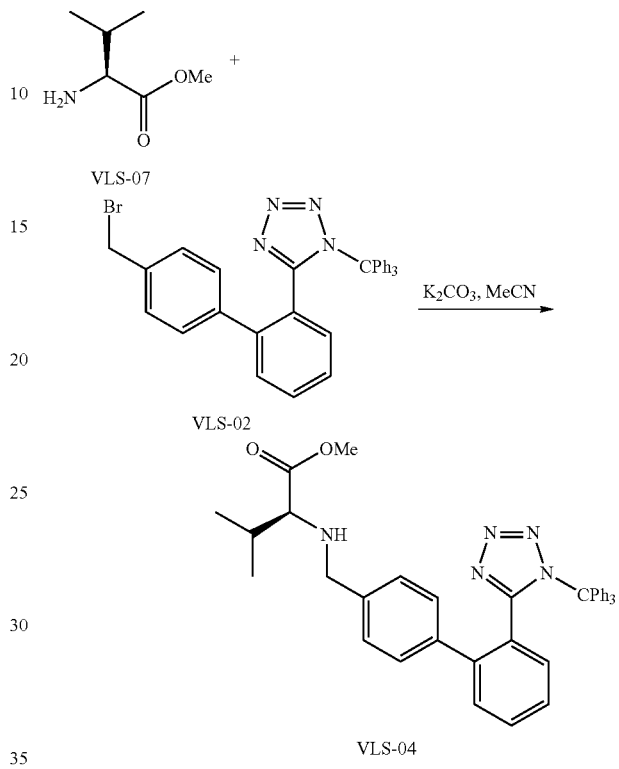

To a suspension of L-valine methyl ester (free base, VLS-07, 4.8 g, 36.3 mmol) and $K_2CO_3$ (10.0 g, 72.6 mmol, 2 eq) in anhydrous acetonitrile (100 mL) was added VLS-02 (18.2 g, 32.7 mmol, 0.9 eq) in three portions. The reaction was stirred for 3.5 hours at 70° C. under argon (TLC monitoring; hexane/ethyl acetate 4:1), cooled to 0° C. and filtered. The filtrate was evaporated under reduced pressure to give 23.0 g of crude VLS-04 as a sticky yellow oil, having a purity of 75–80%, as determined by HPLC.

EXAMPLE 2

Preparation of VLS-05

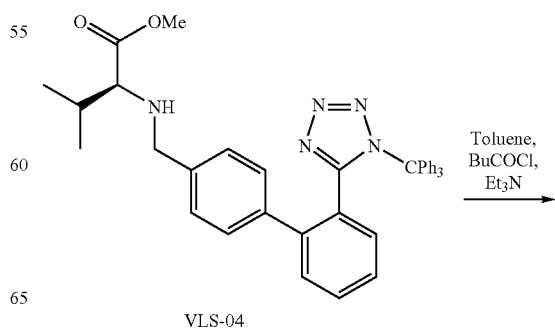

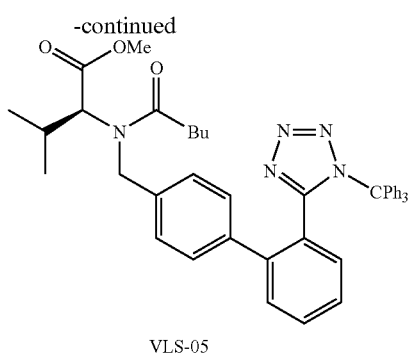

VLS-05

To solution of VLS-04 (prepared in Example 1, used without further purification; 75% purity, 23.0 g, 28.4 mmol) and triethylamine (5.2 g, 7.2 mL, 51.12 mmol, 1.8 eq) in dry toluene (200 mL) was slowly added valeroyl chloride (4.8 g, 4.7 mL, 39.8 mmol, 1.4 eq) under Argon. The resulting mixture was stirred for 20 hours at room temperature (TLC monitoring; hexane/ethyl acetate 4:1) and subsequently quenched with a 10% aqueous solution of $NaHCO_3$ (100 mL). The reaction mixture was stirred for an additional 30 min at room temperature, after which the two-phase mixture was separated. The organic phase was washed with brine, dried over $Na_2SO_4$, filtered and evaporated under reduced pressure to give 25.0 g of crude VLS-05 (about 75% purity by HPLC) as a yellow semisolid. The crude VLS-05 product was purified on a short silica gel column (hexane/ethyl acetate 8:1) to give 15.8 g (80% yield based on VLS-02; 95% purity by HPLC) of VLS-05 as a yellow foam.

EXAMPLE 3

Preparation of Valsartan (VLS-00)

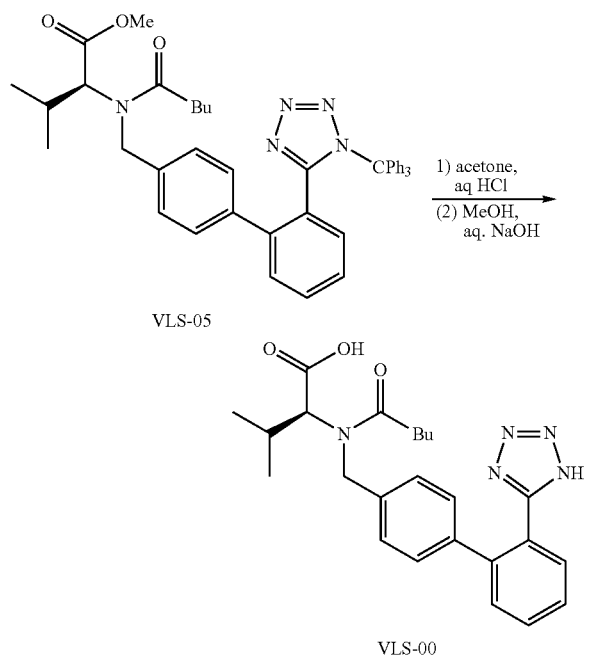

VLS-05 (15.0 g, 21.7 mmol), produced in Example 2, was dissolved in acetone (90 mL) and 3N HCl (22 mL, approx. 3 eq), and stirred for 5 hours at room temperature (with TLC or HPLC monitoring). A solution of KOH (85%, 5.8 g, 86.8 mmol, 4 eq) in 50 mL of water was slowly added, and the acetone was evaporated under reduced pressure. Trityl alcohol precipitate was filtered and washed with water (20 mL), and the combined aqueous filtrate washed with 50 mL of ethyl acetate and slowly acidified to pH 3 with 3N aqueous HCl. The resulting suspension was extracted twice with ethyl acetate, and the organic layers combined, washed with brine, and evaporated under reduced pressure to give 8.8 g (approx. 90% yield) of crude VLS-06.

The residue was redissolved in methanol (80 mL), cooled to 0–4° C. and treated with a 5% aqueous solution of KOH (65 mL, 49.0 mmol, ~2.5 eq). The resulting mixture was stirred for 5 hours at room temperature (with TLC and HPLC monitoring), and most of the methanol evaporated under reduced pressure. The aqueous solution was extracted with ethyl acetate (2×30 mL), and slowly acidified to pH 3 with 3N aqueous HCl. The resulting suspension was cooled down to 0–4° C., stirred for 30 min and filtered. The filter cake was washed with several portions of water, and dried under reduced pressure at 40–50° C. to give 7.6 g (81% based on VLS-05; 96–98% purity by HPLC) of VLS-00 as a white solid.

EXAMPLE 4

Preparation of VLS-04

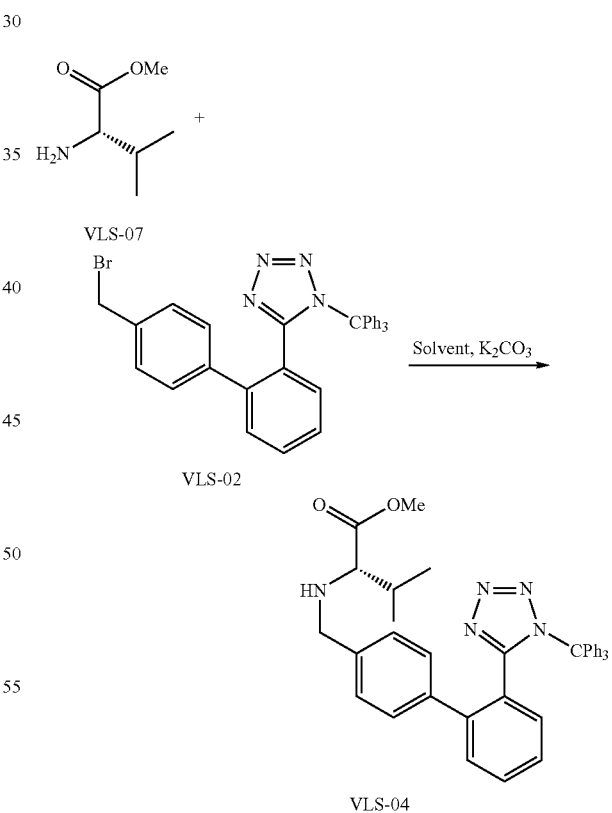

1) Toluene as a Solvent (Liquid-solid Phase Transfer Procedure):

VLS-07 (free base, 2.00 g, 15.3 mmol, 1.5 eq), $Bu_4NHSO_4$ (Phase transfer, 1.56 g, 4.6 mmol, 0.3 eq) and $K_2CO_3$ (8.5 g, 61.2 mmol, 6 eq) were heated to 85–90° C. in dry Toluene (25 mL) under Argon and solution of VLS-02

(5.66 g, 10.2 mmol) in dry Toluene (30 mL) was added during 1.5 h period. The resulted suspension was vigorously stirred at 85–90° C. for 4 h (TLC monitoring, Hex/EtOAc 4:1) and then cooled to 0–4° C. The precipitate was filtered and the filtrate was evaporated under reduced pressure to give 7.0 g (near quant.) of crude VLS-04 (85% purity about HPLC) as yellow viscous oil. The crude was used in the next step without any purification (The crude VLS-04 was also purified on a silica gel column to give 75% yield of VLS-04 with 95% purity by HPLC).

2) Acetonitrile as a Solvent:

VLS-07 (free base, 2.00 g, 15.3 mmol, 1.5 eq) and $K_2CO_3$ (7.05 g, 51.0 mmol, 5 eq) were heated to 70° C. in dry acetonitrile (25 mL) under Argon and VLS-02 (5.66 g, 10.2 mmol) was added in one portion. The resulted suspension was vigorously stirred at 70° C. for 2.5 h (TLC monitoring, Hex/EtOAc 4:1) and then cooled to 0–4° C. The precipitate was filtered and the filtrate was evaporated under reduced pressure to give 7.0 g (near quant.) of crude VLS-04 (85% purity about HPLC) as yellow viscous oil. The crude was used in the next step without any purification (The crude VLS-04 was also purified on a silica gel column to give 75% yield of VLS-04 with 95% purity by HPLC).

Second Step:

The crude VLS-04 from the previous step (7.0 g, ~10 mmol) and $Et_3N$ (3.04 g, 4.18 mL, 30.1 mmol, 3 eq) were dissolved in dry Toluene (50 mL) under Argon and Valeroyl chloride (2.77 g, 2.72 mL, 23.0 mmol, 2.3 eq) was added dropwise at room temperature. The resulted suspension was stirred 5–6 h (TLC monitoring, Hex/EtOAc 4:1) at room temperature and quenched with 10% aqueous $NaHCO_3$ (60 mL). The two-phase mixture was vigorously stirred for 30 min, the phase were separated and organic one washed with brine, dried over $Na_2SO_4$, filtered and evaporated to give about 8.0 g of crude VLS-05 (~80% purity by HPLC).

One-Pot Procedure:

VLS-07 (free base, 2.00 g, 15.3 mmol, 1.5 eq), $Bu_4NHSO_4$ (Phase transfer, 1.56 g, 4.6 mmol, 0.3 eq) and $K_2CO_3$ (8.5 g, 61.2 mmol, 6 eq) were heated to 85–90° C. in dry Toluene (25 mL) under Argon and solution of VLS-02 (5.66 g, 10.2 mmol) in dry Toluene (30 mL) was added during 1.5 h period. The resulted suspension was vigorously stirred at 85–90° C. for 4 h (TLC monitoring, Hex/EtOAc 4:1) and then cooled to 0–4° C. The precipitate was filtered, the filtrate was mixed with $Et_3N$ (3.04 g, 4.18 mL, 30.1 mmol, 3 eq) under Argon and Valeroyl chloride (2.77 g, 2.72 mL, 23.0 mmol, 2.3 eq) was added dropwise at room temperature. The resulted suspension was stirred 5–6 h (TLC monitoring, Hex/EtOAc 4:1) at room temperature and quenched with 10% aqueous $NaHCO_3$ (60 mL). The two-phase mixture was vigorously stirred for 30 min, the phase were separated and organic one washed with brine, dried over $Na_2SO_4$, filtered and evaporated to give about 8.0 g of crude VLS-05 (~70–75% purity by HPLC).

EXAMPLE 5

Preparation of VLS-00 from VLS-05

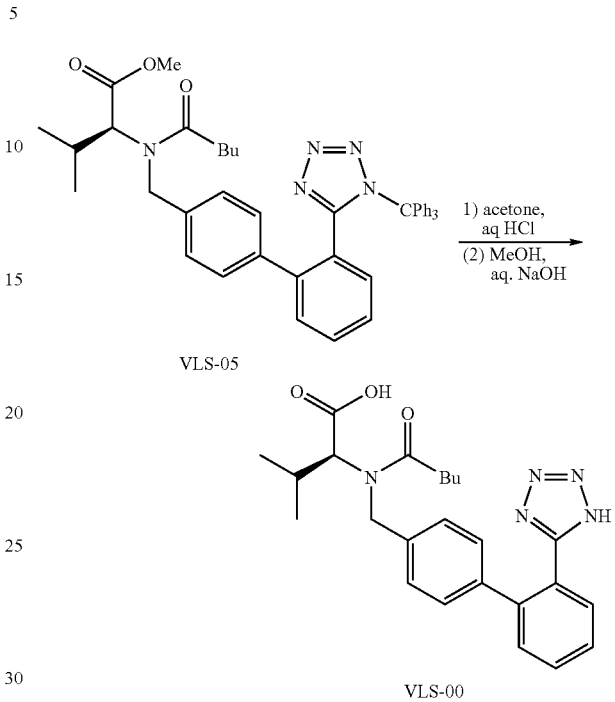

1. Two Step Procedure via VLS-06:

VLS-05 was converted to VLS-00 as follows: VLS-05 (15.0 g, 21.7 mmol) was dissolved in acetone (90 mL) and 3N HCl (22 mL, ~3 eq) and stirred for 5 h at room temperature (TLC or HPLC monitoring). A solution of KOH (85%, 5.8 g, 86.8 mmol, 4 eq) in 50 mL of water was slowly added and acetone was evaporated under reduced pressure. The precipitate (Trityl alcohol) was filtered and washed with water (20 mL); the combined aqueous filtrate washed with 50 mL of EtOAc and slowly acidified to pH 3 with 3N aqueous HCl. The resulted suspension was extracted twice with EtOAc, the combined organics were washed with brine and evaporated under reduced pressure to give 8.8 g (~90% yield) of crude VLS-06. The residue was re-dissolved in MeOH (80 mL), cooled to 0–4° C. and treated with 5% aqueous solution of KOH (65 mL, 49.0 mmol, ~2.5 eq). The resulted mixture was stirred for 5 h at room temperature (TLC and HPLC monitoring) and most of the MeOH was evaporated under reduced pressure. The aqueous solution was extracted with EtOAc (2×30 mL) and slowly acidified to pH 3 with 3N aqueous HCl. The resulted suspension was cooled down to 0–4° C., stirred for 30 min and filtered. The cake was washed several times with water and dried under reduced pressure at 40–50 C and crystallized from Hex/EtOAc 1:2 afforded 7.1 g (75% based on VLS-05, 96–98% chemical purity by HPLC) of VLS-00 as a white solid.

2. One-pot Procedure:

VLS-05 (15.0 g, 21.7 mmol) was dissolved in acetone (90 mL) and 3N HCl (22 mL, ~3 eq) and stirred for 5 h at room temperature (TLC or HPLC monitoring). A solution of KOH (85%, 6.1 g, 108.5 mmol, 5 eq) and $Bu_4NHSO_4$ (0.75 g, 2.2 mmol, 0.1 eq) in 60 mL of water was slowly added, the resulted suspension was stirred for 24 h at room temperature and Acetone was evaporated under reduced pressure. The precipitate (Trityl alcohol) was filtered and washed with water (20 mL); the combined aqueous filtrate washed with 50 mL of EtOAc and slowly acidified to pH 2 with 6 N aqueous HCl. The resulted suspension was extracted twice with EtOAc (total 120 mL), the combined organics were washed with brine and concentrated to 50 mL volume under reduced pressure. This solution was cooled down to 0–4 C, stirred for 5 h and filtered to give 7.2 g (75% based on VLS-05, 97% chemical purity by HPLC) of VLS-00 as a white solid.

EXAMPLE 6

Preparation of Valsartan using EtOAc as a Solvent

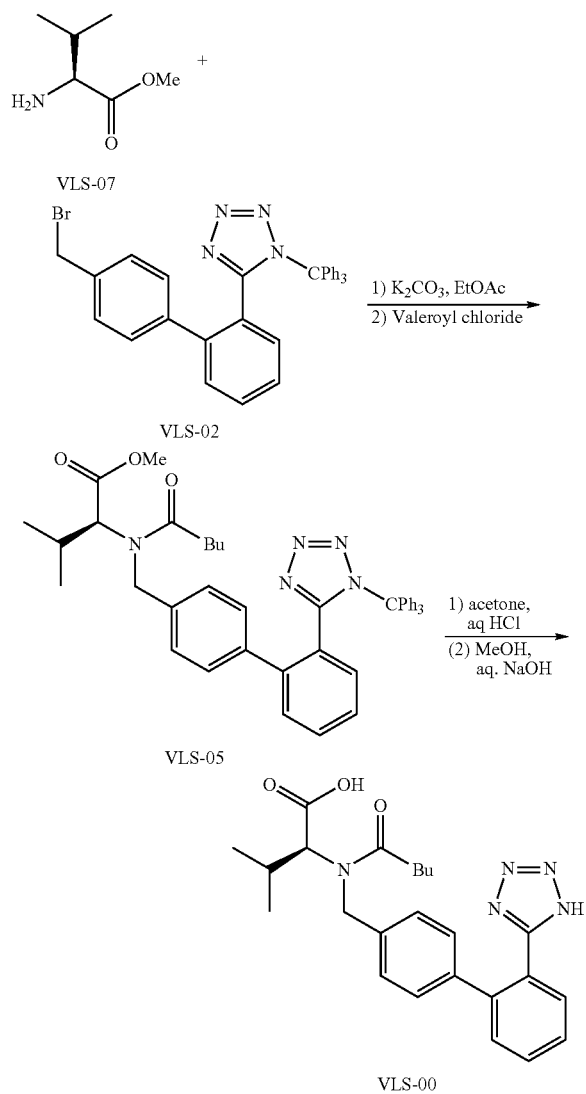

To a suspension of L-valine methyl ester (free base, VLS-07, 5.0 g, 36.5 mmol, 1.5 eq) and $K_2CO_3$ (28 g, 203 mmol, 8 eq) in dry EtOAc (150 mL), VLS-02 (14.2 g, 25.5 mmol) was added in one portion. The reaction was stirred for 20–24 h at reflux temperature under argon (TLC monitoring; Hex/EtOAc 4:1), cooled to 0° C., followed by addition of valeroyl chloride (7.3 g, 7.2 mL, 61.0 mmol, 2.4 eq). The resulting suspension was stirred for 2 hours at room temperature (TLC monitoring; Hex/EtOAc 4:1) and quenched with Water (200 mL). After stirring of 1 h at room temperature, the two-phase mixture was separated, the organic phase washed with water and evaporated under reduced pressure to give 20.5 g of crude VLS-05 (about 90–95% purity by HPLC) as yellow foam. VLS-05 (20.5 g, ~25.5 mmol) was dissolved in acetone (100 mL) and 3N HCl (25 mL, ~3 eq), and stirred for 5 hours at room temperature.

A solution of NaOH (6.1 g, 152.5 mmol, 6 eq) in 15 mL of water was slowly added and the resulting yellow solution was stirred for 10 h at room temperature and 4 hours at 50° C. Water (70 mL) was added, acetone was evaporated under reduced pressure and the precipitate (trityl alcohol) was filtered and washed with water (2×30 mL); the combined aqueous filtrate washed with EtOAc (2×30 mL) and slowly acidified to pH 2.5–3.5 with concentrated HCl. The resulting suspension was extracted twice with EtOAc (total 200 mL), the combined organics were washed with brine dried over $Na_2SO_4$, filtered and evaporated under reduced pressure to 60 mL volume. Hexane (20 mL) was added and the resulting solution was vigorously stirred at 0–5° C. for 2–3 hours. The suspension was filtered, the solid washed with cold mixture Hexane/EtOAc (1:1, 2×20 mL) and dried under reduced pressure at 50° C. until constant weight to give 7.7 g (~70% yield for 4 steps) of crude VLS-00 as white powder.

EXAMPLE 7

Trituration of Valsartan

Valsartan (5 grams, contained 2.7% of EtOAc) was suspended in 50 mL of water and stirred for 12 hours at 40° C. The suspension was filtered, washed with water and the solid was dried for 3 hours at 35° C. under reduced pressure to give 4.9 g of valsartan as a white powder.

EXAMPLE 8

Hydrolysis and Cleaning of Trityl Valsartan

A solution of 98% sulfuric acid (1.45 g, 14.75 mmol) in water (30 mL) was added at 23–27° C. to a suspension of trityl valsartan, containing 7.97% of D-trityl valsartan, (10 g, 14.75 mmol) in acetone (60 mL). The obtained suspension was stirred at 23–27° C. for about 24 h. The suspension was basified with 3 N solution of sodium hydroxide to pH 11.7–11.9. Acetone was then distilled off and the precipitated solids so-formed were filtered off and washed with water (6 mL×2). The combined water layers were extracted with ethyl acetate (18 mL×2), the water solution was acidified with 3 N solution of sulfuric acid to pH 2.5–2.7, extracted with ethyl acetate (36 mL×3), dried over sodium sulfate, filtered and evaporated to give a semi-solid residue (3.9 g) of VLS, containing 0.40% of D-VLS.

EXAMPLE 9

Cleaning D-isomer During the Reaction

A solution of 98% Sulfuric acid (1.45 g, 14.75 mmol) in Water (30 mL) was added to a solution of TVLS, containing about 4% of D-TVLS, (10 g, 14.75 mmol) in Acetone (60 mL), and the suspension formed was stirred at 15–25° C. for about 24 h. After this, the suspension was basified with 3 N solution of Sodium Hydroxide to pH 11.7–11.9, Acetone was removed under reduced pressure at 30° C., Triphenyl-carbinol was filtered off and washed with Water (6 mL×2), the basic aqueous solution was extracted with Ethyl Acetate (18 mL×2), acidified with 3 N Solution of Sulfuric acid to pH 2.6–28, extracted with Ethyl Acetate (36 mL×3), the Ethyl Acetate solution was washed with brine (20 mL), dried over Sodium sulfate and evaporated to give a solid residue of VLS (3.92 g, 61%) containing 0.59% of D-VLS.

EXAMPLE 10

Hydrolysis and Cleaning of Trityl Valsartan

Trityl valsartan (5.0 g) was mixed with methanol (50 mL) and the suspension was heated to reflux to give a solution which was refluxed for about 1 h (TLC monitoring, DCM/Methanol 7:1). The solution was heated at this temperature for an additional 1.5 h. The solution was then cooled to 20–25° C. and stirred for about 1 h at this temperature. Thee precipitated solids were filtered off and the filtrate was kept overnight at 4–8° C. and then at −13° C. for about 1 h. The precipitated solids were filtered off; the filtrate was evaporated to give a semisolid residue (2.25 g, 70%). The level of the D-isomer was 0.4%

EXAMPLE 11

Hydrolysis and Cleaning of Trityl Valsartan

To clear yellow solution of Valsartan Trityl (400 g, ~80% assay, ~0.50 mol) containing 4% of D-trityl valsartan in Acetone (1600 mL, 5 volumes), $H_2SO_4$ (98%, 73.5 g, 40.0 mL, 0.75 mol) dissolved in $H_2O$ (450 mL, 1.5 volumes) was slowly added keeping reaction temperature in range 35–40° C. The resulted suspension (the suspension disappeared after 1–1.5 h of stirring) was stirred for 3h at 35–40° C. (TLC monitoring; Hex/EtOAc 1:1), cooled to room temperature and slowly basified to pH 12.0–12.5 with NaOH (~4.5 eq, 90.0 g, 2.25 mol) dissolved in $H_2O$ (600 mL). Acetone was evaporated under reduced pressure at 30° C. and the resulted precipitate (triphenyl carbinol) was filtered and washed with $H_2O$ (200 mL). The combined aqueous phase was extracted with EtOAc (500 mL) and acidified to pH 2–3 with 3M $Na_2SO_4$ (~300 mL). The acidic aqueous suspension was extracted with EtOAc (2200 mL), the organic phase was dried over $Na_2SO_4$ (200 g) and evaporated under reduced pressure. The sticky semisolid residue (~400 g) containing 3.8% D-trityl valsartan was crystallized from EtOAc (1500 mL, solution at 60° C., start of precipitation at 23° C., then 15 h at 20–21° C. and 1 h at 0–4° C.). The precipitate was filtered, washed with cold (−5° C.) EtOAc (200 mL) and dried under reduced pressure at 50° C. for 1 h to give 193 g of crude Valsartan as white solid containing 0.38% D-trityl valsartan. The crude was recrystallized from EtOAc (1500 mL, solution at 63° C., start of precipitation at 27° C., then 15 h at 20–21° C. and 1 h at 0–4° C.) to give ~150 g of Valsartan crystals as white powder. Valsartan crystals were triturated with $H_2O$ (1500 mL) for 24 h at 30° C., filtered, washed with $H_2O$ (2×200 mL) and dried on the filter for 1 h (Valsartan after trituration contains ~25% (w/w) of H2O). Then, Valsartan was dried under reduced pressure (10–13 mmHg) at 50° C. for 5 h (KF ~0.9%) to give 142 g (71–72% yield) of the desired product (VLS-303–07, assay 99.8% by titration) as white powder. The D isomer detected in the final product (USP forum 2003 method) is 0.07%. The isoleucine impurity was detected by HPLC at a level of 0.01% area.

EXAMPLE 12

Hydrolysis and Cleaning of Trityl Valsartan

A solution of 98% Sulfuric acid (1.45 g, 14.75 mmol) in Water (30 mL) was added to a solution of TVLS, containing about 4% of D-TVLS, (10 g, 14.75 mmol) in Acetone (60 mL), and the suspension formed was stirred at 15–25° C. for about 24 h. After this, the suspension was basified with 3 N solution of Sodium Hydroxide to pH 11.7–11.9, Acetone was removed under reduced pressure at 30° C., Triphenylcarbinol was filtered off and washed with Water (6 mL×2), the basic aqueous solution was extracted with Ethyl Acetate (18 mL×2), acidified with 3 N Solution of Sulfuric acid to pH 2.6–28, extracted with Ethyl Acetate (36 mL×3), the Ethyl Acetate solution was washed with brine (20 mL), dried over Sodium sulfate and evaporated to give a solid residue of VLS (3.92 g, 61%) containing 0.59% of D-VLS.

EXAMPLE 13

Process for the Preparation of Valsartan, Starting from Trityl Valsartan

TVLS (10.0 g, 14.75 mmol) was dissolved at reflux in Methanol (100 mL) and the solution was refluxed for about 3 h (TLC control). The solution was cooled to 20–25° C. and basified with 3 N aqueous solution of Sodium hydroxide to pH 11.8. Methanol was removed under reduced pressure at 30° C., the precipitate was filtered off and washed on the filter with Water (6 mL×2). The aqueous filtrate was extracted with ethyl acetate (14 mL×2) and acidified with 3 N solution of Sulfuric acid to pH 2.7. The precipitated viscous oil was extracted with Ethyl Acetate (18 mL×3), the combined extracts were washed with brine (20 mL), dried over Sodium sulfate and evaporated to give a solid residue of VLS, (4.81 g, 74.9%). The level of the D-isomer was 3.85%.

EXAMPLE 14

Hydrolysis and Cleaning of Trityl Valsartan

TVLS (5.0 g) was dissolved in Methanol (50 mL) at reflux and the solution was refluxed for about 1 h (TLC control). Methanol was removed under reduced pressure to obtain a residue (10 g). The residue was kept overnight at 4–7° C., the precipitate was filtered off, the filtrate evaporated to give the solid residue of VLS (2.89 g, 89.5%). The level of the D-isomer was 4.4%.

EXAMPLE 15

Hydrolysis and Cleaning of Trityl Valsartan

A 10 liter reactor equipped with mechanical stirrer, condenser and thermometer, was charged at ambient temperature with trityl valsartan (1 Kg ), acetone (4 L) and an aqueous mixture of $H_2SO_4$ 98% ($H_2SO_4$:$H_2O$ 100 mL: 1125 mL). The slurry was then heated to 36° C. and stirred at a rate of 400 rpm for 5 hours until the end of the reaction (monitoring by TLC).

The slurry was then cooled to 22–24° C. and was basified with a mixture of NaOH flakes (243 g ) and water (1620 cc ) while maintaining the temperature below 28° C. At the end of the addition the temperature was 23° C. and the pH was 12.5. The reactor jacket was then heated to 40° C., and the acetone of the reaction mixture was distilling off under vacuum (40–200 mm Hg). The distillation lasted 4 hours and the jacket was then cooled to 30° C. The triphenyl carbinol that precipitated during the distillation was filtered and washed with water (500 mL). The mother liquor so obtained (3930 g) was returned to the reactor and EtOAc (1250 mL) was added and stirred for 30 minutes, then the stirring was stopped for 30 minutes and the separation of the two phases was performed. The aqueous phase (4083 g) was returned to the reactor and was acidified with an aqueous mixture of $H_2SO_4$ 98% ($H_2SO_4$: water 150 g: 417 mL) while maintaining the temperature below 25° C. At the end of the addition the temperature was 25° C. and the pH was 2.5. EtOAc (5500 mL) was then added and stirred for 30 minutes, then the stirring was stopped for 30 minutes and a phase separation was performed. To the organic phase (~6600 g), sodium sulfate (Na2SO4 450 g) was added, stirred in the reactor for 20 minutes and then the reactor content was filtered under vacuum. The organic phase was returned to the reactor and a distillation was performed under vacuum (10–200 mm Hg) at 40° C. The distillation lasted 6.5 hours leading to a solid residue in the reactor. Then the vacuum was stopped and EtOAc (3750 mL) was added while the reactor was heated to 50° C. until getting a clear solution. The heating was continued for 0.5 hours. Then the clear solution was cooled to 32–34° C. and seeded with 0.5 g of Valsartan. At the end of the addition the stirring was maintained for 0.5 hours at 32–34° C., then cooled during 2 hours until 22–24° C. and maintained while stirring for 0.5 hours at this temperature. The slurry was then cooled during 2 hours until 0–2° C. and maintained while stirring for 0.5 hours at this temperature. The suspension was then filtered, washed with EtOAc (500 mL) to obtain 630.3 g of wet material.

EXAMPLE 16

Preparation of Valsartan Crystals

A 10 liter reactor equipped with mechanical stirrer, condenser and thermometer, was charged with Valsartan crude wet (630 g) and EtOAc (3700 mL). The jacket was then heated to 45° C. and stirred at a rate of 400 rpm until getting a clear solution. The heating was continued for 0.5 hours. Then the clear solution was cooled to 34–36° C. and seeded with 0.1 g of VLS. At the end of the addition the stirring was maintained for 0.5 hours at 34–36° C., then cooled during 2 hours until 24–26° C. and maintained while stirring for 0.5 hours at this temperature. The slurry was then cooled during 2.5 hours until 0° C. (±5° C.) and maintained while stirring for 0.5 hours at this temperature. The slurry was then filtered and washed with EtOAc (400 mL) to obtain 549.3 g of wet material.

EXAMPLE 17

Drying the Wet Valsartan with Vacuum Dryer while Stirring 600 g of Valsartan prepared according to example 38 were put in the drying apparatus while heating to 45° C. under vacuum (less than 60 mm Hg). The solid was maintained for 2 hours without stirring, and then the stirrer was put on (15–20 rpm) for about 7 hours until the loss on drying reach not more than 2%. The XRD pattern showed that the material is essentially amorphous, and the DSC showed an endotherm with enthalpy 29 J/g.

EXAMPLE 18

Drying the Wet Valsartan with Vacuum Dryer while Stirring then Humidification with Humid Nitrogen 600 g of Valsartan prepared according to example 38 were put in the drying apparatus while heating to 45° C. under vacuum (less than 60 mm Hg). The solid was maintained for 2 hours without stirring, and then the stirrer was put on (15–20 rpm) for about 4 hours until the loss on drying reach 6.5%. 60 g of the so obtained solid was put in a 0.5 L reactor at 50° C. under stirring (20 rpm). To this solid was flowed humidified nitrogen during 2 hours. Then the nitrogen was stopped and the solid was put under vacuum (less than 30 mm Hg) for 3 hours. The vacuum was stopped and humidified nitrogen was flowed inside the reactor for 2 hours (humidification of the nitrogen was done by bubbling nitrogen through a vessel of water). Then the nitrogen was stopped again and the solid was put again under vacuum (less than 30 mm Hg) for 5 hours. The XRD pattern showed that the material is essentially amorphous, and the DSC showed an endotherm with enthalpy 29 J/g

EXAMPLE 19

Drying the Wet Valsartan with Vacuum Dryer while Stirring then Humidification with Fluidized Bed 85 g of the material obtained in example 39 (after drying with stirring and LOD=2%) was put in the fluidized bed at 30–40° C. during 13 hours. The XRD pattern showed that the material is essentially amorphous, and the DSC showed an endotherm with enthalpy 29 J/g.

EXAMPLE 20

Harsh Drying 10 g of Valsartan with loss on drying less than 10% are dried under vacuum oven (1 mm Hg) at 60° C. for 24 hours to get a compound with loss on drying less than 0.5%.

EXAMPLE 21

Harsh Drying 10 g of Valsartan with loss on drying less than 10% are dried under vacuum oven (50 mm Hg) at 30° C. for 5 days to get a compound with loss on drying less than 0.5%.

EXAMPLE 22

Harsh Drying 10 g of Valsartan with loss on drying less than 10% are dried under vacuum oven (40 mm Hg) at 20° C. for 5 days to get a compound with loss on drying less than 0.5%.

Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications.

What is claimed is:

1. A process for preparing valsartan containing less than about 5000 ppm residual solvent, comprising the steps of:
   a) providing valsartan containing less than about 10% organic solvent by weight;
   b) triturating the valsartan in water, or contacting the valsartan with humid air in a fluidized bed drier, or maintaining the valsartan at a temperature of from about 5 to about 60° C. under pressure of less than about 30 mmHg for a period of from about 1 to 5 days; and
   c) recovering the valsartan containing less than about 5000 ppm residual solvent.

2. The process of claim 1, wherein the valsartan of step (b) is prepared by triturating the valsartan in water.

3. The process of claim 2, wherein the valsartan of step (b) is triturated in about 4 to about 30 volumes of water per 1 gr of valsartan, for a period of time of about 5 and about 48 hours.

4. The process of claim 3, wherein the valsartan prepared has less than about 0.10% of D-isomer.

5. The process of claim 4, wherein the D-isomer is present at about 0.07% as area percentage HPLC.

6. The process of claim 1, wherein the valsartan of step (b) is prepared by contacting the valsartan with humid air in a fluidized bed drier.

7. The process of claim 6, wherein the atmosphere in the fluidized bed drier is at least 30% humidity.

8. The process of claim 1 wherein the valsartan of step (b) is prepared by maintaining the valsartan at a temperature of from about 5 to about 60° C. under pressure of less than about 30 mmHg for a period of from about 1 to 5 days.

9. The process of claim 8, wherein the valsartan of step (b) is maintained under pressure of less than about 10 mmHg.

10. The process of claim 9, wherein the valsartan of step (b) is maintained under pressure of less than about 1 mmHg.

11. The process of claim 2, 6 or 8 wherein the organic solvent is selected from the group consisting of: ethyl acetate, butyl acetate, diisopropyl acetate, dichloromethane and acetone.

12. The process of claim 11, wherein the organic solvent is ethyl acetate.

13. The process of claims 2, 6 or 8 wherein the valsartan of step (b) is dried at a temperature of from about 5 to about 60° C.

14. The process of claims 2, 6 or 8 wherein the valsartan of step (a) is obtained by drying until the organic solvent content is of less than about 10% by weight.

15. The process of claim 14, wherein the valsartan that is dried is obtained by crystallization from an organic solvent.

16. The process of claims 2, 6 or 8 wherein the valsartan of step (a) is obtained by crystallization from an organic solvent.

17. The process of claims 16, wherein the organic solvent is selected from the group consisting of: ethyl acetate, butyl acetate, diisopropyl acetate, dichloromethane and acetone.

18. The process of claim 17, wherein the organic solvent is ethyl acetate.

* * * * *

UNITED STATES PATENT AND TRADEMARK OFFICE
CERTIFICATE OF CORRECTION

PATENT NO.          : 7,199,144 B2
APPLICATION NO.  : 10/829873
DATED                    : April 3, 2007
INVENTOR(S)          : Rukhman et al.

Page 1 of 1

It is certified that error appears in the above-identified patent and that said Letters Patent is hereby corrected as shown below:

Column 25, line 3, change "pH 2.6 – 28" to -- pH 2.6 – 2.8 --
Column 26, line 15, change "pH 2.6 – 28" to -- pH 2.6 – 2.8 --
Column 27, line 60, change "example 38" to -- example16 --
Column 28, line 6, change "example 38" to -- example16 --
Column 28, line 29, change "example 39" to -- example17 --

Signed and Sealed this

Eighth Day of December, 2009

David J. Kappos
*Director of the United States Patent and Trademark Office*